United States Patent
Lin et al.

(10) Patent No.: US 10,466,199 B2
(45) Date of Patent: Nov. 5, 2019

(54) BIOSENSOR DEVICE

(71) Applicant: NATIONAL TAIWAN UNIVERSITY, Taipei (TW)

(72) Inventors: Chih-Ting Lin, Taipei (TW); Shey-Shi Lu, Taipei (TW); Yu-Hao Chen, Taipei (TW); Sheng-Yeh Chou, Taipei (TW); I-Shun Wang, New Taipei (TW); Che-Wei Huang, Taoyuan (TW); Pei-Wen Yen, New Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 272 days.

(21) Appl. No.: 15/391,889

(22) Filed: Dec. 28, 2016

(65) Prior Publication Data

US 2017/0184541 A1    Jun. 29, 2017

Related U.S. Application Data

(60) Provisional application No. 62/271,327, filed on Dec. 28, 2015.

(51) Int. Cl.
*G01N 27/00* (2006.01)
*G01N 33/48* (2006.01)
*G01N 25/18* (2006.01)
*H01L 29/66* (2006.01)
*G01N 27/414* (2006.01)
*G01N 33/52* (2006.01)

(52) U.S. Cl.
CPC ..... *G01N 27/4148* (2013.01); *G01N 27/4145* (2013.01); *G01N 33/525* (2013.01)

(58) Field of Classification Search
CPC ........ G01N 27/00; G01N 33/48; G01N 25/18; H01L 29/66
USPC ..... 422/68.1, 82.01, 82.02; 436/43, 63, 149; 257/27, 47, 69, 121, 124, 133, 187, 192, 257/197, 205
See application file for complete search history.

(56) References Cited

U.S. PATENT DOCUMENTS

| | | | |
|---|---|---|---|
| 2013/0105868 A1* | 5/2013 | Kalnitsky | G01N 27/414 257/288 |
| 2013/0200438 A1* | 8/2013 | Liu | G01N 27/414 257/253 |
| 2014/0175435 A1* | 6/2014 | Yamazaki | H01L 29/78618 257/43 |
| 2014/0264467 A1* | 9/2014 | Cheng | G01N 27/4145 257/253 |
| 2017/0059514 A1* | 3/2017 | Hoffman | G01N 33/5438 |
| 2017/0067890 A1* | 3/2017 | Lin | H01L 51/0093 |

* cited by examiner

*Primary Examiner* — Brian J. Sines
(74) *Attorney, Agent, or Firm* — Bacon & Thomas, PLLC

(57) ABSTRACT

A biosensor device includes a substrate, a sensing transistor, an isolation layer and a main interface layer. The sensing transistor is formed on the substrate and including a bottom gate structure, a top gate structure and a semiconductor layer disposed between the bottom gate structure and the top gate structure. The bottom gate structure is electrically connected to the top gate structure. The isolation layer is formed on the sensing transistor for covering the sensing transistor, and includes a first opening. The main interface layer is disposed in the first opening for receiving biomolecules to be sensed. The main interface layer is electrically connected to the top gate structure.

20 Claims, 5 Drawing Sheets

BIOSENSOR DEVICE

CROSS REFERENCE TO RELATED APPLICATION

This application claims the benefit of filing date of U. S. Provisional Application Ser. No. 62/271,327, entitled "MOLECULE SENSOR DEVICE" filed Dec. 28, 2015 under 35 USC § 119(e)(1).

BACKGROUND OF THE INVENTION

1. Field of the Invention

The present invention relates to a sensor, and more particularly, to a biosensor device.

2. Description of Related Art

Biosensors are expected for measurements in biological features such as corpuscles, proteins, carbohydrates, antibodies or metal ions. Biosensors are advantageous for their high specificity, high sensitivity and high selectivity, and are applicable in the fields of medicine, biological technology, food, agriculture and environment monitoring.

There are several types of biosensors, for example, electrochemical biosensor, semiconductor ion sensor, fiber-optic biosensor and piezoelectric quartz crystal biosensor. FIG. 1 shows a prior sensor device 1. In the fabrication of the prior sensor device 1, a silicon oxide (SiO2) layer 12 is disposed on a poly layer 11. A bulk 13 covers the SiO2 layer 12 and the poly layer 11. The bulk 13 and the SiO2 layer 12 are etched to form a well 14. The poly layer 11 is used as a sensing element. However, in the manufacture of the prior sensor device 1, the bulk 13 needs to be etched for a large depth which is difficult to control, and there should be another process for etching the SiO2 layer 12. Moreover, since the etching of the SiO2 layer 12 is inconsistent with the standard CMOS fabrication, it is difficult to control the remaining thickness of the SiO2 layer 12, and as a result, the yield factor of the prior sensor device 1 varies.

Therefore, it is desirable to provide an improved biosensor to mitigate or obviate the aforementioned problems.

SUMMARY OF THE INVENTION

An object of the present invention is to provide a biosensor device that can improve the sensitivity by enhancing the sensing signal strength and removing the environmental noise interference.

Another object of the present invention is to provide a biosensor device that can be manufactured in the standard CMOS fabrication, so as to reduce the manufacturing cost.

To achieve the objects, the biosensor device according to the present invention includes a substrate; a sensing transistor formed on the substrate and including a bottom gate structure, a top gate structure and a semiconductor layer disposed between the bottom gate structure and the top gate structure, the bottom gate structure being electrically connected to the top gate structure; an isolation layer formed on the sensing transistor for covering the sensing transistor, and including a first opening; and a main interface layer disposed in the first opening for receiving biomolecules to be sensed, the main interface layer being electrically connected to the top gate structure.

Other objects, advantages, and novel features of the invention will become more apparent from the following detailed description when taken in conjunction with the accompanying drawings.

DETAILED DESCRIPTION OF THE PREFERRED EMBODIMENT

Different embodiments according to the present invention are provided in the following description. It is to be understood that the embodiments are not meant to be limiting. Other embodiments can be utilized by arranging, substituting, combining, separating, and designing the features according to the present invention.

First Embodiment

Figure 2:
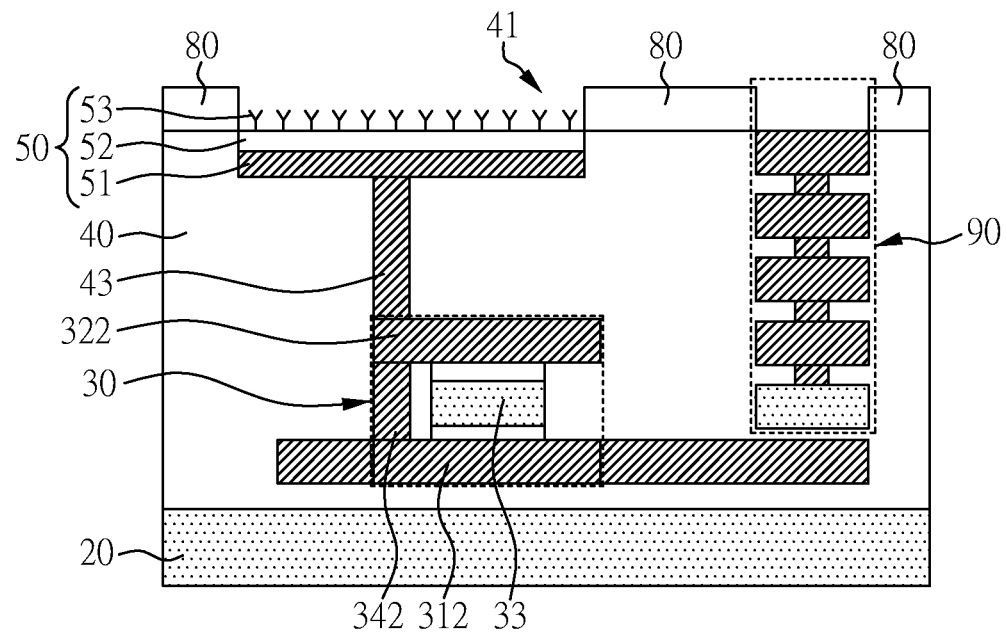
FIG. 2 shows the first embodiment of the biosensor device according to the present invention.

FIG. 2 shows the first embodiment of the biosensor device 2 according to the present invention. The biosensor device 2 includes a substrate 20, a sensing transistor 30, an isolation layer 40, and a main interface layer 50.

The substrate 20 can be made of semiconductor materials such as Si, Ge, SiC, GaAs, GaP, InP, InAs, InSb, SiGe, GaAsP, AlInAs, AlGaAs, GaInAs, GaInP, GaInAsP, or the combinations thereof.

The sensing transistor 30 is formed on the substrate 20.

Figure 3:
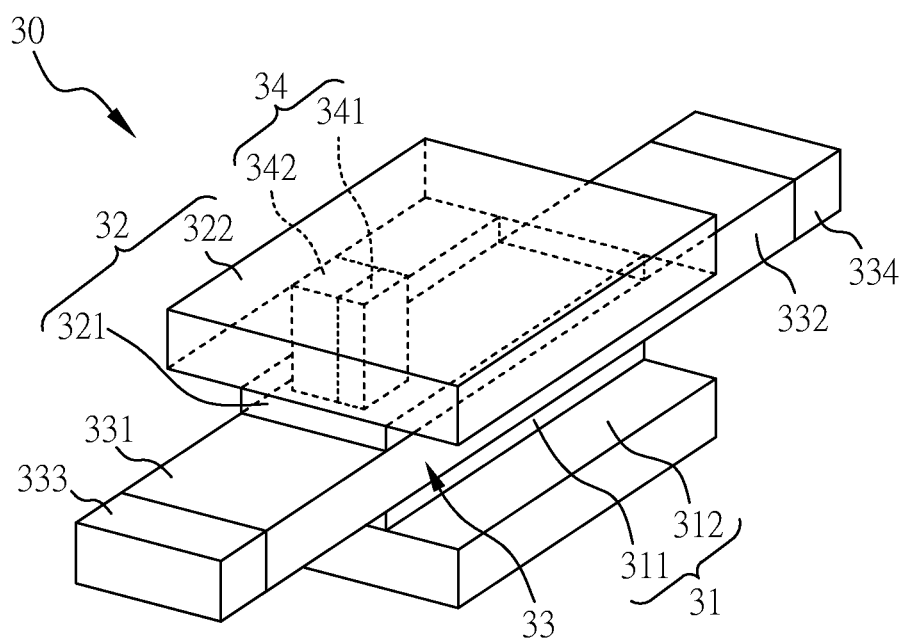
FIG. 3 shows a perspective view of the sensing transistor in the first embodiment of the present invention.

To further describe the details of the semiconductor layer 33, FIG. 3 shows a perspective view of the sensing transistor 30 in the first embodiment of the present invention.

The sensing transistor 30 includes a bottom gate structure 31 with a bottom dielectric layer 311 and a bottom conductive layer 312, a top gate structure 32 with a top dielectric layer 321 and a top conductive layer 322, and a semiconductor layer 33. The bottom conductive layer 312 of the bottom gate structure 31 is electrically connected to the top conductive layer 32 of the top gate structure 32 through a first via hole 34. The first via hole 34 is coated with a dielectric material 341 and then filled with a conductive material 342. The semiconductor layer 33 is electrically isolated to the bottom conductive layer 312, the top conductive layer 322 and the conductive material 342 by the bottom dielectric layer 311, the top dielectric layer 321 and the dielectric material 341, respectively. Accordingly, the bottom gate structure 31, the top gate structure 32 and the first via hole 34 constitute a C-shaped gate structure of the sensing transistor 30.

The semiconductor layer 33 can be made of the semiconductor materials as previously described for the substrate 20. Moreover, without being limited to crystalline materials (such as c-Si), the semiconductor materials may include polycrystalline materials (such as poly-Si) and amorphous materials (such as a-Si).

The bottom dielectric layer 311, the top dielectric layer 321 and the dielectric material 341 can be made of dielectric materials such as silicon oxide, silicon nitride, silicon oxynitride, a dielectric with a high dielectric constant (high-k), or the combinations thereof.

The bottom conductive layer 312, the top conductive layer 322 and the conductive material 342 can be made of conductive materials such as Cu, W, Ti, Ta, Cr, Pt, Ag, Au, TiN, TaN, NiSi, CoSi, doped semiconductor materials (as previously described for the substrate 20) or the combinations thereof.

As shown in FIG. 3, the semiconductor layer 33 is shaped as a wire, and it is regarded as a semiconductor wire. However, the semiconductor layer 33 is not limited to be shaped as a wire.

In this case, the semiconductor layer 33 includes a source portion 331 connected to a source electrode 333 at one end of the semiconductor wire, and a drain portion 332 connected to a drain electrode 334 at the other end of the semiconductor wire. The source electrode 333 and the drain electrode 334 are further connected to a sensing circuit (not shown). The sensing circuit may determine the existence of the biomolecules or the properties of the biomolecules.

As shown in FIG. 3, the source portion 331 and the drain portion 332 can be protruded beyond the region covered by the bottom gate structure 31, the top gate structure 32, the first via hole 34 and the second via hole 35. In other words, the bottom gate structure 31, the top gate structure 32 and the first via hole 34 only cover a portion of the semiconductor layer 33, which is regarded as a covered portion.

Referring back to FIG. 2, the isolation layer 40 covers the sensing transistor 30 and the substrate 20. The isolation layer 40 includes a first opening 41 on its surface.

The main interface layer 50 for receiving biomolecules to be sensed is disposed in the first opening 41. The main interface layer 50 includes a main interface conductive layer 51 at its bottom and a receptor layer 53 at its top. The main interface conductive layer 51 is electrically connected to the top conductive layer 322 of the top gate structure 32 through a third via hole 43. The receptor layer 53 is used to receive the biomolecules to be sensed. Preferably, the main interface layer 50 includes a main interface interlayer 52 disposed between the main interface conductive layer 51 and the receptor layer 53 to protect the main interface conductive layer 51 from chemical erosion or electrical discharge. The main interface interlayer 52 can be made of conductive materials or dielectric materials as previously discussed.

The main interface conductive layer 51 and the third via hole 43 can be made of the conductive materials as previously described.

The receptor layer 53 can be formed by coating enzymes, antibodies, ligands, receptors, peptides, nucleotides, cells of organs, organisms or pieces of tissue, depending on the species of the biomolecules to be sensed. The receptor layer 53 can immobilize (or capture) the biomolecules to be sensed.

It is noted that, in FIG. 2, the top surface of the main interface layer 50 is substantially coplanar with a top surface of the isolation layer 40. This implies that, in the present invention, the isolation layer 40 only needs to be etched for the depth of the interface layer 50. In other words, the first opening 41 is a shallow opening of a small depth suitable for receiving the interface layer 50. This is advantageous in comparison with the prior art shown in FIG. 1, wherein the poly layer 11 is at the bottom of the well 14, and the bulk 13 and the SiO2 layer 12 needs to be etched for a large depth which is difficult to control.

Figure 1:
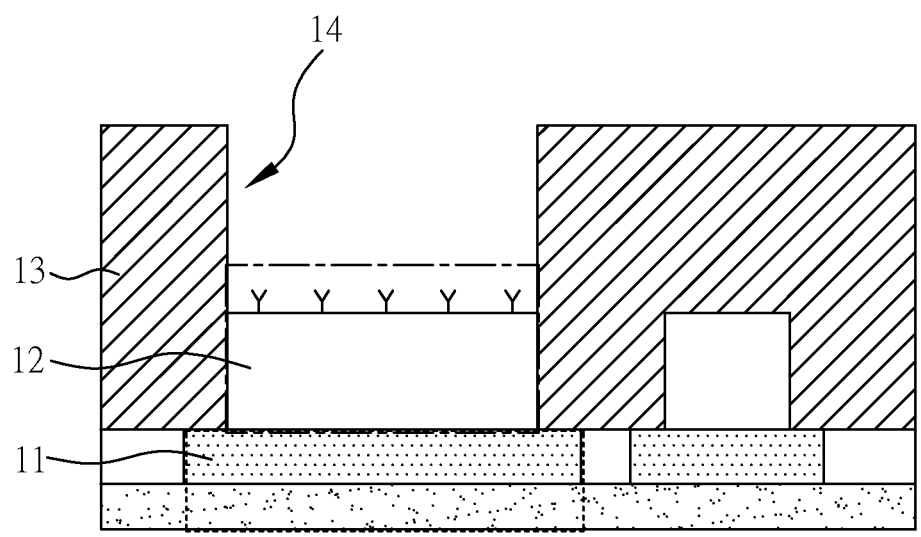
FIG. 1 shows a prior sensor device.

In another aspect, in the present invention, the main interface interlayer 52 can be disposed after the first opening 41 is formed, so that it is easier to manufacture the main interface interlayer 52 of the present invention than the SiO2 layer 12 of the prior art shown in FIG. 1.

In operation, when being received by the receptor layer 53, the biomolecules to be sensed will induce an electric field on the main interface layer 50, and the electric field will cause changes of electrical properties such as voltage, current, capacitance or resistance on the main interface conductive layer 51. The interface conductive layer 51 will then generate a gate signal to be sent to the top gate structure 32 (the top conductive layer 322) as well as to the bottom gate structure 31 (the bottom conductive layer 322) through the first via hole 34 (the conductive material 342).

According to the gate signal applied on the C-shaped gate structure composed of the bottom gate structure 31, the top gate structure 32 and the first via hole 34, the sensing transistor 30 can be turned on or turned off, so as to output a sensing signal. Then, the sensing signal will be sent to the sensing circuit to determine the existence of the biomolecules or the properties of the biomolecules.

With the C-shaped gate structure, the gate signal can be uniformly applied to three sides of the semiconductor layer 33, and a stronger electrical field effect can be induced in the semiconductor layer 33. Thus, the sensitivity of the biosensor device 2 can be improved.

The main structure and the main function of the first embodiment are described as above.

Several preferable or optional features in the first embodiment are provided in the following description.

As shown in FIG. 2 the biosensor device 2 includes an insulating wall layer 80 surrounding the first opening 41. The insulating wall 80 can be made of the dielectric material as previously described, or it can be made of plastic such as Cytop, TEFLON or Parylene. The insulating wall layer 80 is used to hold the matter including the biomolecules to be sensed.

Moreover, as shown in FIG. 2, the biosensor device 2 includes a multilayer interconnection (MLI) structure 90, and a part of the isolation layer 40 is included in the multilayer interconnection structure 90. A part of the via hole 43 and a part of the main interface conductive layer 41 can also be included in the multilayer interconnection structure 90 since the manufacturing are consistent with the standard CMOS fabrication.

Further, as shown in FIG. 2, the center of the first opening 41 is not aligned with the center of the sensing transistor 30. That is, the first opening 41 is dislocated with the sensing transistor 30 from a top view of the biosensor device 2. With such a dislocation, there can be additional space to receive additional components, such as a control layer which will be described hereinafter. This is advantageous in comparison with the prior art shown in FIG. 1, wherein there is no more space remained above the poly layer 11 (which serves as the sensing element).

Second Embodiment

Figure 4:
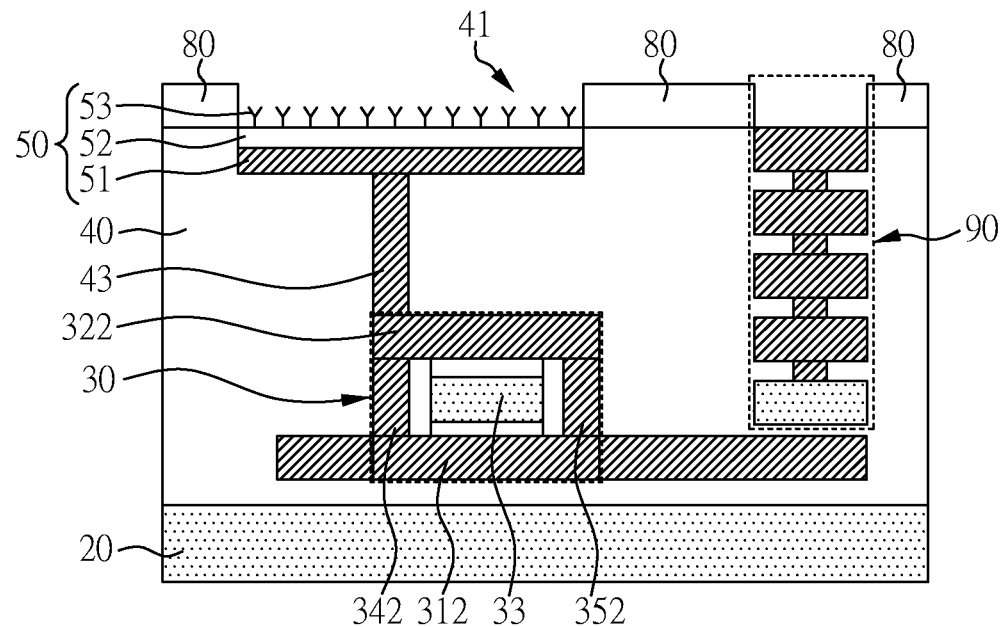
FIG. 4 shows the second embodiment of the biosensor device according to the present invention.

FIG. 4 shows the second embodiment of the biosensor device 2 according to the present invention. The second embodiment is provided on the basic of the first embodiment. However, in the second embodiment, the bottom conductive layer 312 is electrically connected to the top conductive layer 322 through not only the first via hole 34, but also a second via hole 35. The second via hole 35 is coated with a dielectric material 351 and then filled with a conductive material 352. Accordingly, the bottom gate structure 31, the top gate structure 32, the first via hole 34 and the second via hole 35 vertically surround the semiconductor layer 33, and constitute a surrounding gate structure of the sensing transistor 30.

Figure 5:
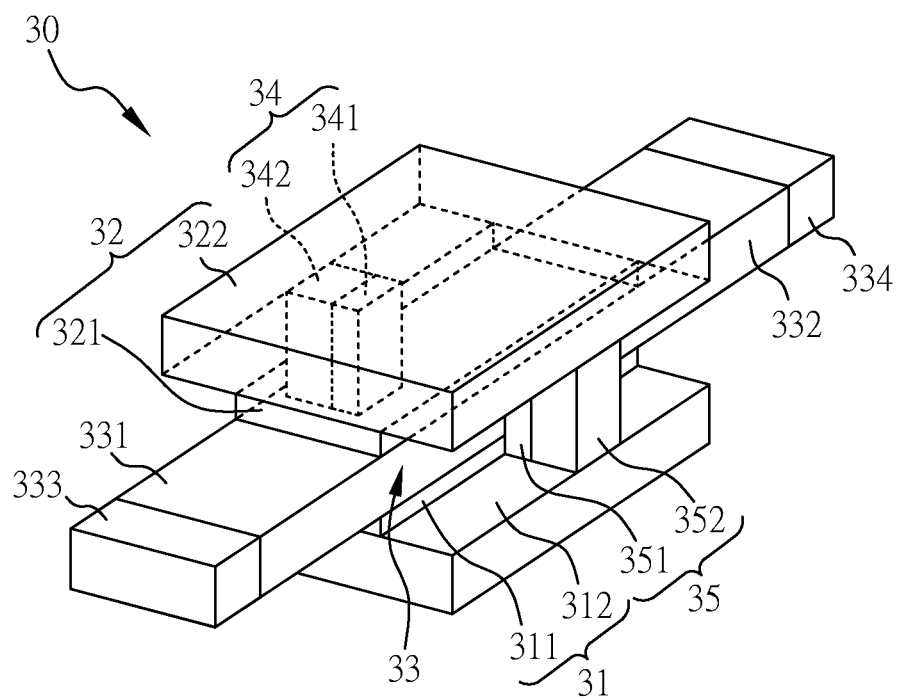
FIG. 5 shows a perspective view of the sensing transistor in the second embodiment of the present invention.

FIG. 5 shows a perspective view of the sensing transistor 30 in the second embodiment of the present invention. The structure of the semiconductor layer 33 in FIG. 5 is similar to that in FIG. 3, except that the existence of the second via hole 35. In this case, the bottom gate structure 31, the top gate structure 32, the first via hole 34 and the second via hole 35 only surround a portion of the semiconductor layer 33, which is regarded as a surrounded portion.

The second embodiment is advantageous in that: since the bottom conductive layer 312 and the top conductive layer 322 are connected through two paths, the via hole 34 and the second via 35, the resistance of the connection between the bottom conductive layer 312 and the top conductive layer 322 can be reduced, and the strength of the gate signal can be maintained.

Moreover, with the surrounding gate structure composed of the bottom gate structure 31, the top gate structure 32, the first via hole 34 and the second via hole 35, the gate signal can be uniformly applied to four sides of the semiconductor layer 33, and a stronger electrical field effect can be induced in the semiconductor layer 33. Thus, the sensitivity of the biosensor device can be improved.

Third Embodiment

Figure 6:
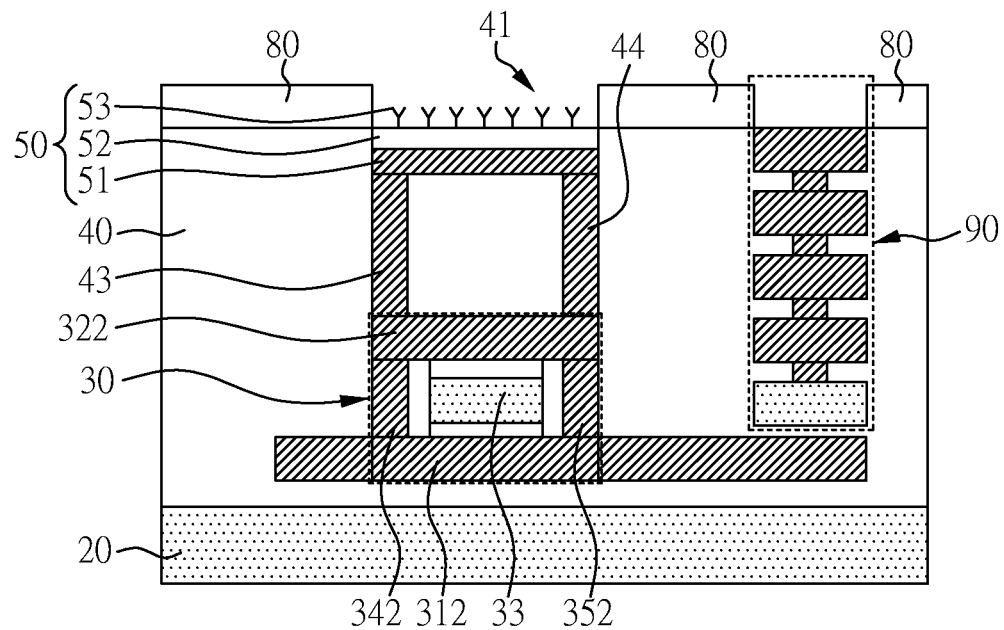
FIG. 6 shows the third embodiment of the biosensor device according to the present invention.

FIG. 6 shows the third embodiment of the biosensor device 2 according to the present invention. The third embodiment is provided on the basic of the second embodiment. However, in the third embodiment, the main interface conductive layer 51 is electrically connected to the top conductive layer 322 through not only the third via hole 43, but also a fourth via hole 44. Thus, the resistance of the connection between the first conductive layer 51 and the top conductive layer 322 can be reduced, and the strength of the gate signal can be maintained.

Fourth Embodiment

Figure 7:
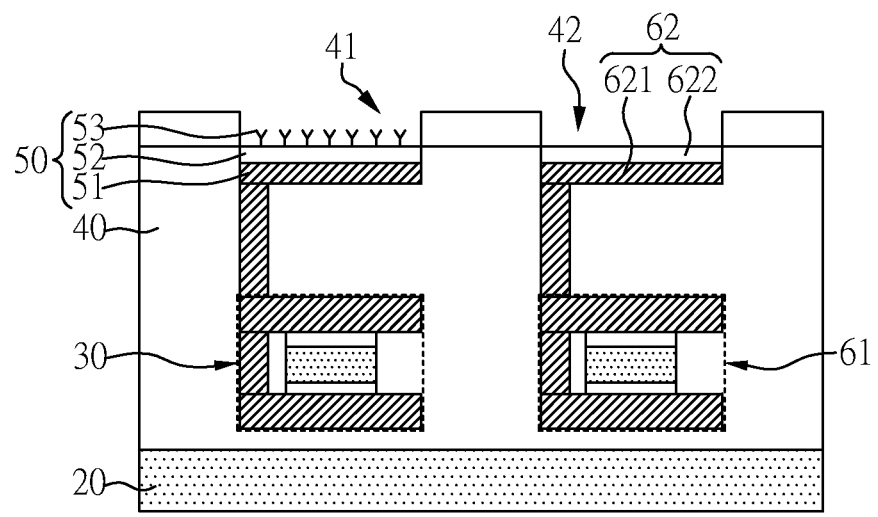
FIG. 7 shows the fourth embodiment of the biosensor device according to the present invention.

FIG. 7 shows the fourth embodiment of the biosensor device 2 according to the present invention. The fourth embodiment is provided on the basic of the first embodiment, but it is also applicable to other embodiments.

It is known that a sensing performed by a biosensor device may be interfered by environments. The same sensing performed by the same biosensor device may have different results in different environments. Herein, the environment is referred to the solvent (which can be liquid, gas or solid) including the biomolecules to be sensed. In other words, the environmental factors cause sensing inaccuracy. Thus, in the present invention, reference components are considered to be incorporated with the sensing components (that is, the components described in the first embodiment) in the biosensor device 2, in order to remove environmental factors.

Accordingly, in the fourth embodiment, the biosensor device 2 is further provided with a set of reference components 60. The reference components 60 include a reference transistor 61 and a reference interface layer 62.

The reference interface layer 62 is formed on the surface of the isolation layer 40, so that it can come into touch with the environment.

The reference interface layer 62 includes a second conductive layer 621. However, it is noted that the reference interface layer 62 excludes a receptor layer, so that the reference interface layer 62 is incapable of immobilizing (or capturing) the biomolecules to be sensed, and thus it only senses the electric field induced by the environment rather than the electric field induced by the biomolecules to be sensed.

The reference interface conductive layer 621 of the reference interface layer 62 is electrically connected to a gate of the reference transistor 61 through a via hole or via holes.

In operation, the electric field induced by the environment will cause changes of electrical properties such as voltage, current, capacitance or resistance on the reference interface conductive layer 621. The reference interface conductive layer 621 then generates a reference gate signal to the gate of the reference transistor 61 for enabling the reference transistor 61 to output a reference signal.

The reference signal can be compared with the sensing signal in a comparator or a differential amplifier. By subtracting the reference signal from the sensing signal, the environment factors can be removed.

In order to provide more accurate reference signal, the reference transistor 61 is preferably formed of similar (preferably the same) structure or materials to the sensing transistor 30, for example, with a C-shaped gate structure or a surrounding gate structure.

Preferably, the reference interface 62 is formed of similar (preferably the same) structure or materials to the main interface layer 50. For example, the reference interface layer 62 can be formed in a second opening 42 on the surface of the isolation layer 40, wherein the second opening 42 is separated from the first opening 41, and the reference interface 62 is substantially coplanar with the main interface layer 50. Moreover, the reference interface layer 62 includes a reference interface interlayer 622 disposed on the reference interface conductive layer 621 to protect the reference interface conductive layer 721 from chemical erosion or electrical discharge.

Further, the reference components 60 including the reference transistor 61 and the reference interface 62 can be formed simultaneously with the sensing component including the sensing transistor 30 and the main interface layer 50 in the same manufacturing process, except that the reference interface layer 62 excludes a receptor layer.

With the similarity, the reference components 60 and the sensing components will be interfered by the environment simultaneously in a similar way, and such interference can be cancelled out.

Fifth Embodiment

Figure 8:
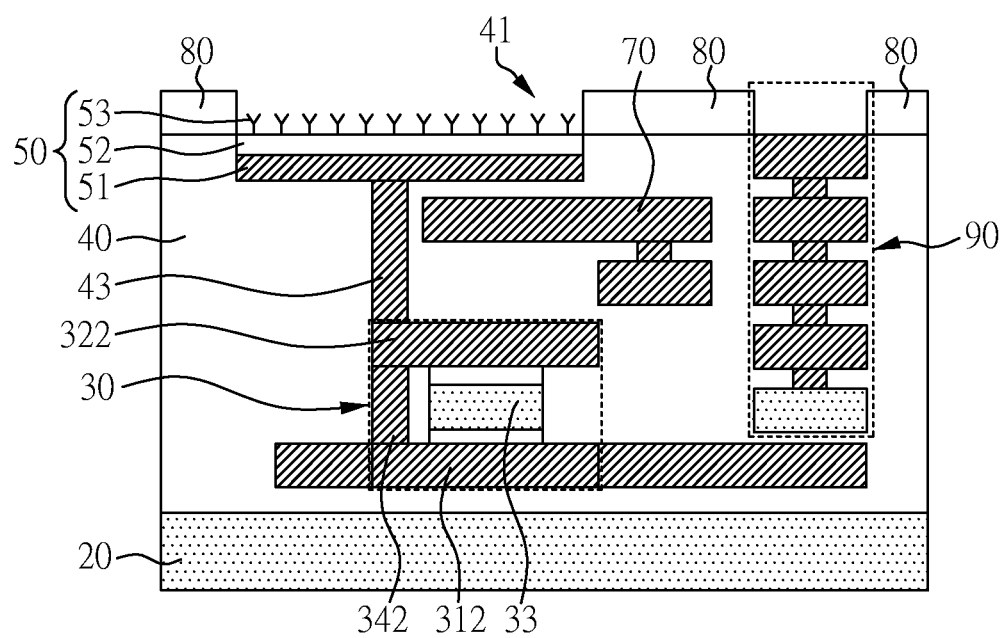
FIG. 8 shows the fifth embodiment of the biosensor device according to the present invention.

FIG. 8 shows the fifth embodiment of the biosensor device 2 according to the present invention. The fifth embodiment is provided on the basic of the first embodiment, but it is also applicable to the other embodiments.

In the fifth embodiment, the biosensor device 2 further includes a control layer 70 under and near the first opening 41. The control layer is electrically isolated to the main interface conductive layer 51 of the main interface layer 50, so that it is also electrically isolated to the other components electrically connected to the main interface conductive layer 51, such as the top conductive layer 322.

The control layer 70 is made of conductive materials as previously described.

In operation, the control layer 70 is applied with an independent control voltage that induces an electric field to attract the biomolecules to be sensed. After a sufficient amount of the biomolecules to be sensed has fallen on the interface layer 50, the independent control voltage should be turned off, so that the independent control voltage will not interfere the sensing. Then, the sensing can start.

As described above, the present invention has provided a biosensor device that can improve the sensitivity by enhancing the sensing signal strength and removing the environmental noise interference. The biosensor device according to the present invention can be manufactured in the standard CMOS fabrication, and thus the manufacturing cost can be reduced.

Although the present invention has been explained with the aforementioned embodiment, it is to be understood that many other modifications and variations can be made without departing from the spirit and scope of the invention as hereinafter claimed.

What is claimed is:

1. A biosensor device, comprising:
   a substrate;
   a sensing transistor formed on the substrate and including a bottom gate structure, a top gate structure and a semiconductor layer disposed between the bottom gate structure and the top gate structure, the bottom gate structure being electrically connected to the top gate structure;
   an isolation layer formed on the sensing transistor for covering the sensing transistor, wherein the isolation layer includes a first opening; and
   a main interface layer disposed in the first opening for receiving biomolecules to be sensed, the main interface layer being electrically connected to the top gate structure.

2. The biosensor device as claimed in claim 1, wherein the bottom gate structure further includes a bottom conductive layer and a bottom dielectric layer disposed between the bottom conductive layer and the semiconductor layer, and the top gate structure further includes a top conductive layer and a top dielectric layer disposed between the top conductive layer and the semiconductor layer.

3. The biosensor device as claimed in claim 1, wherein the bottom gate structure is electrically connected to the top gate structure through a first via hole electrically isolated to the semiconductor layer.

4. The biosensor device as claimed in claim 3, wherein the bottom gate structure is electrically connected to the top gate structure through a second via hole electrically isolated to the semiconductor layer, and the bottom gate structure, the top gate structure, the first via hole and the second via hole vertically surround a surrounded portion of the semiconductor layer.

5. The biosensor device as claimed in claim 4, wherein the semiconductor layer further includes a source portion connected to a source electrode; and a drain portion connected to a drain electrode, wherein the source portion and the drain portion are out of the surrounded portion of the semiconductor layer.

6. The biosensor device as claimed in claim 1, wherein the semiconductor layer is a semiconductor wire with one end serving as a source portion connected to a source electrode and another the other end serving as a drain portion connected to a drain electrode.

7. The biosensor device as claimed in claim 1, wherein the first opening is dislocated with the sensing transistor from a top view of the biosensor device, wherein a center of the first opening is not aligned with a center of the sensing transistor.

8. The biosensor device as claimed in claim 1, wherein the main interface layer further includes an main interface conductive layer electrically connected to the top gate structure, and a receptor layer formed on the main interface first conductive layer for receiving the biomolecules to be sensed.

9. The biosensor device as claimed in claim 8, wherein the main interface layer further includes a main interface interlayer disposed between the main interface conductive layer and the receptor layer.

10. The biosensor device as claimed in claim 8, wherein the receptor layer includes enzymes, antibodies, ligands, receptors, peptides, nucleotides, cells of organs, organisms or pieces of tissue.

11. The biosensor device as claimed in claim 1, wherein the main interface layer is electrically connected to the top gate structure through a third via hole at one end of the main interface layer and a fourth via hole at another end of the main interface layer.

12. The biosensor device as claimed in claim 1, wherein a top surface of the main interface layer is coplanar with a top surface of the isolation layer.

13. The biosensor device as claimed in claim 1, wherein the biomolecules to be sensed induce a gate signal in the top gate structure and the bottom gate structure for enabling the transistor to output a sensing signal.

14. The biosensor device as claimed in claim 13, further comprising a reference transistor for outputting a reference signal to be compared with the sensing signal.

15. The biosensor device as claimed in claim 14, further comprising:
   a second opening separated from the first opening on the isolation layer; and
   a reference interface layer without receptors in the second opening, the reference interface layer inducing the reference transistor to output the reference signal.

16. The biosensor device as claimed in claim 15, wherein the reference interface layer is coplanar with the main interface layer.

17. The biosensor device as claimed in claim 15, wherein the reference transistor and the sensing transistor are formed of same structure.

18. The biosensor device as claimed in claim 1, further comprising a multilayer interconnection structure including the isolation layer.

19. The biosensor device as claimed in claim 1, further comprising an insulating wall layer surrounding the first opening.

20. The biosensor device as claimed in claim 1, further comprising a control layer under the first opening, the control layer being electrically isolated to the main interface layer, and applied with an independent control voltage.

* * * * *